(12) United States Patent
Kraus et al.

(10) Patent No.: US 6,340,361 B1
(45) Date of Patent: Jan. 22, 2002

(54) EXTERNAL FIXATOR CLAMP AND SYSTEM

(76) Inventors: Karl H. Kraus, 20 Blackstone St., Sutton, MA (US) 01590; Harold M. Wotton, III, 544 Main St., Fiskdale, MA (US) 01518

( * ) Notice: Subject to any disclaimer, the term of this patent is extended or adjusted under 35 U.S.C. 154(b) by 0 days.

(21) Appl. No.: 09/388,875

(22) Filed: Sep. 2, 1999

Related U.S. Application Data

(62) Division of application No. 08/841,529, filed on Apr. 23, 1997, now Pat. No. 5,976,133.

(51) Int. Cl.⁷ .................................................. A61B 17/58
(52) U.S. Cl. ........................................ 606/59; 606/54
(58) Field of Search .......................... 606/54, 55, 57, 606/59, 96, 102, 104

(56) References Cited

U.S. PATENT DOCUMENTS

| | | | | |
|---|---|---|---|---|
| 2,267,157 A | * | 12/1941 | Lippincott | 606/56 |
| 2,372,866 A | | 4/1945 | Tofflemire | 128/76 |
| 2,391,537 A | | 12/1945 | Anderson | 128/84 |
| 2,391,693 A | | 12/1945 | Ettinger | 128/84 |
| 3,547,113 A | * | 12/1970 | Swanson | 606/54 |
| 3,727,610 A | * | 4/1973 | Riniker | 606/55 |
| 3,985,127 A | * | 10/1976 | Volkov et al. | 606/55 |
| 4,235,428 A | * | 11/1980 | Davis | 606/96 |
| 4,257,411 A | * | 3/1981 | Cho | 606/96 |
| 4,338,927 A | * | 7/1982 | Volkov et al. | 606/55 |
| 4,360,012 A | * | 11/1982 | McHarrie et al. | 606/56 |
| 4,573,459 A | * | 3/1986 | Litton | 606/56 |
| 4,628,919 A | | 12/1986 | Clyburn | 128/92 |
| 4,768,524 A | * | 9/1988 | Hardy | 606/56 |
| 4,901,711 A | * | 2/1990 | Goble et al. | 606/98 |
| 5,002,542 A | | 3/1991 | Frigg | 606/61 |
| 5,098,432 A | | 3/1992 | Wagenknecht | 606/54 |
| 5,207,676 A | | 5/1993 | Canadell et al. | 606/54 |
| 5,275,599 A | | 1/1994 | Zbikowski et al. | 606/54 |
| 5,292,322 A | | 3/1994 | Faccioli et al. | 606/59 |

(List continued on next page.)

FOREIGN PATENT DOCUMENTS

| | | | | |
|---|---|---|---|---|
| CH | 638 390 | | 9/1983 | A61B/17/18 |
| DE | 2.069 846 A | | 9/1981 | A61B/17/18 |
| DE | 91 03 480.9 | | 7/1991 | A61B/17/56 |
| EP | 0 194 187 | | 9/1986 | A61B/17/60 |
| EP | 0 707 832 A1 | | 4/1996 | A61B/17/60 |

OTHER PUBLICATIONS

Ebix Fix, DynaFix™ System, DFS™ Standard Fixator, Operative Technique, Brochure. (No Date Given).
Synthes Price List 1995, Synthes (USA) P.O. Box 1766, 1690 Russell Road, Paoli, PA 19301–0800 (8/92) (Brochure).

(List continued on next page.)

*Primary Examiner*—Henry J. Recla
*Assistant Examiner*—(Jackie) Tan-Uyen T. Ho
(74) *Attorney, Agent, or Firm*—Hamilton, Brook, Smith & Reynolds, P.C.

(57) ABSTRACT

An external fixator system comprises a clamp adapted to couple a fixator pin to a connecting rod. The clamp includes a slot for transversely receiving the connecting rod. A bolt is inserted through a bore passing transversely to the slot to engage a pin connector holding a fixator pin. The pin connector has a rod-engaging surface that wedges the connecting rod into the slot thus increasing the clamp's rigidity by preventing rotation of the clamp around the rod and rotation of the pin connector in the clamp body. An aiming device is also disclosed, which attaches to at least two connecting rods to guide the insertion of fixator pins between the rods. The aiming device is adjustable to accommodate various distances between the rods and has different modes of attachment to the rods to enable the clamp installation either above or below the rods.

11 Claims, 10 Drawing Sheets

U.S. PATENT DOCUMENTS

| | | | |
|---|---|---|---|
| 5,304,177 A | 4/1994 | Pennig | 606/58 |
| 5,312,403 A | 5/1994 | Frigg | 606/54 |
| 5,314,426 A | 5/1994 | Pohl et al. | 606/58 |
| 5,320,622 A | 6/1994 | Faccioli et al. | 606/58 |
| 5,320,623 A | 6/1994 | Pennig | 606/59 |
| 5,342,360 A | 8/1994 | Faccioli et al. | 606/59 |
| 5,350,378 A | 9/1994 | Cole et al. | 606/57 |
| 5,391,167 A | 2/1995 | Pong et al. | 606/57 |
| 5,393,161 A | 2/1995 | Mata et al. | 403/133 |
| 5,397,322 A | 3/1995 | Campopiano | 606/57 |
| 5,451,225 A | 9/1995 | Ross, Jr. et al. | 606/59 |
| 5,476,462 A | 12/1995 | Allard et al. | 606/60 |
| 5,624,440 A | 4/1997 | Huebner | 606/59 |
| 5,630,814 A * | 5/1997 | Ross, Jr. et al. | 606/59 |
| 5,683,389 A | 11/1997 | Orsak | 606/59 |
| 5,746,741 A | 5/1998 | Kraus et al. | 606/54 |
| 5,785,709 A * | 7/1998 | Kummer et al. | 606/56 |
| 5,833,691 A * | 11/1998 | Bimman | 606/80 |

OTHER PUBLICATIONS

Slatter, D., "Textbook of Small Animal Surgery," Second Edition, vol. II, pp. 1641–1660 (1995, 1985 by W.B. Saunders Company).

D.P. Brooks, Jr., et al., "Design of a Fastener and Bolt for an External Fixation Device," *Worcester Polytechnic Institute*, submitted in partial fulfillment of the requirements for the Degree of Bachelor of Science, pp. 1–69 (Apr. 28, 1994).

G. Chu, et al., "External Skeletal Fixation," *Worcester Polytechnic Institute*, submitted in partial fulfillment for the Degree of Bachelor of Science, pp. 1–109 (May 1, 1995).

Database, WPI, Section PQ, Week 8346 Dec. 28, 1983, Derwent Publications Ltd., London, GB, Class P31, AN 83–819207 XP002049947 and SU 990 208A (A.N. Edinak), Jan. 28, 1983.

* cited by examiner

EXTERNAL FIXATOR CLAMP AND SYSTEM

RELATED APPLICATIONS

This application is a Divisional application of U.S. application Ser. No. 08/841,529, filed Apr. 23, 1997 U.S. Pat. No. 5,976,133 the entire teachings of which are incorporated herein by reference.

BACKGROUND OF THE INVENTION

External skeletal fixator systems are used on fractured bones or joints during osteosynthesis typically for more serious injuries involving multiple or compound fractures. Pins are drilled through a patient's skin and into a fractured bone. Clamps secure the pins to a common connecting rod, creating a rigid frame that immobilizes the bone.

The Kirschner-Ehmer external fixator system is commonly used in veterinary orthopedic surgery. The system includes: a standard connecting rod; clamps adapted to slide over the ends of the connecting rod; fixator pins; and bolts for tightening the clamps around the connecting bars, which bolts have through-holes near the head for receiving the fixator pins' shafts.

The Kirschner-Ebmer system precludes installation of an additional clamp between two installed clamps on the connecting bar or removal of an intermediate clamp without disassembly of the entire connecting rod. This is because the Kirschner-Ehmer clamp includes a narrow slot leading to a wider channel, into which channel a connecting rod is inserted axially. The connecting rod will not fit into the slot to allow for transverse mounting. Consequently, the surgeon must anticipate the number of clamps required and slide them onto the connecting rod before insertion of the end pins into the bone. This is especially limiting if an additional pin or clamp is required at the completion of surgery or at subsequent patient visits. In addition, the Kirschner-Ehmer clamp undergoes plastic deformation when tightened, permanently deforming and fatiguing the material. Consequently, reuse of the clamp is discouraged. Furthermore, the Kirschner-Ehmer clamp is inapplicable in ring fixators such as the Ilizarov external ring fixator.

A fixator clamp produced by Synthes® permits transverse installation of a clamp on a connecting rod between two installed clamps without rod disassembly. It includes a slot for receiving a connecting rod, a hole for receiving a pin in an orthogonal direction relative to the connecting rod, a clevis-shaped clamp, and a bolt and nut which simultaneously secure the pin in the hole and the clamp on the connecting rod. This design is limited to orthogonal pin placements relative to the connecting rod and is mechanically complex.

The Synthes® and Kirschner-Ehmer designs are particularly susceptible to loosening under repeated cyclic loading. The Kirschner-Ehmer device relies entirely on the axial tension in the bolt to preclude pin rotation. A slight amount of loosening due to cyclic loading reduces axial tension in the bolt, allowing the pin to rotate relative to the connecting rod. The Synthes™ design relies on a clamp that touches the connecting rod at only two points, rendering this device susceptible to loosening.

Improved external fixator clamp designs have been described in U.S. patent application Ser. No. 08/643,512, filed May 6, 1996, entitled "External Fixator System", filed by Kraus, et al., the teachings of which are incorporated herein in their entirely by this reference. There, the clamp body had a slot that was wide enough to transversely receive and snap-fit over the connecting rod. A hook-shaped bolt, rather than the eye-bolt of the Kirschner-Ehmer designs, was used to hold the fixator pin while securing the clamp body to the rod. This configuration enabled the clamp body to be conveniently added in the middle of a rod.

SUMMARY OF THE INVENTION

The present invention is directed to an external fixator clamp that incorporates a number of advantages achieved by the designs described in 08/643,512 application. The present clamp body has a slot that is wide enough to also transversely receive the rod. Innovations, however, are introduced that relieve a number of tolerances in the manufacture of the clamp, thus substantially reducing the per unit cost, while simultaneously increasing the clamp's rigidity.

Rather than a relatively long bolt to secure the pin to the clamp, a pin connector is used that is inserted into a connector bore in the clamp body. This connector has a pin bore for receiving the fixator pin and a rod-engaging surface. The connector is urged into the connector bore until the fixator pin is braced against the clamp body and the rod-engaging surface wedges the connecting rod into the slot to ensure that the rod is seated in the back of the slot. The interference between the connector and rod provides increased resistance to the rotation of the pin relative to the clamp body and rotation of the clamp body relative to the rod. Moreover, since the rod will always be fully seated in the slot by the connector, the clamp body need not snap-fit onto the rod. The snap-fitting functionality required precise manufacturing tolerances in the machining of the slot since the clamp was generally rigid, allowing for only slight amounts of flexing under reasonable forces. In contrast, in the present invention, the slot is preferably machined to the width of the rod.

In the preferred embodiment, a bolt is inserted into a distal end of the connector bore to mate with threads of the pin connector to thereby draw the pin connector into the connector bore. Alternatively, the connector could be externally threaded, but in either case, the connector should have a short overall length to reduce the amount of clearance necessary to couple the connector to the clamp. That is, when the clamp is constructed, the connector extends only partially across the width of the clamp body, the remainder of the distance being covered by the distally inserted bolt or similar fixture.

In general, according to another aspect, the invention also features an aiming device and method to assist in the installation of fixator pins. The device has a frame that is adapted to be attached to first and second connecting rods, between which the pin is to be connected. A guide is provided on the frame to facilitate the pin installation process.

In specific embodiments, the guide may be a bore in the frame or alternatively a sleeve, which is made part of the frame. This guide may provide for pin installation at various angles. The frame is preferably adjustable so that clamps for the pins can be installed either above or below the rods. The frame is also preferably expandable to accommodate various distances between the connecting rods.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
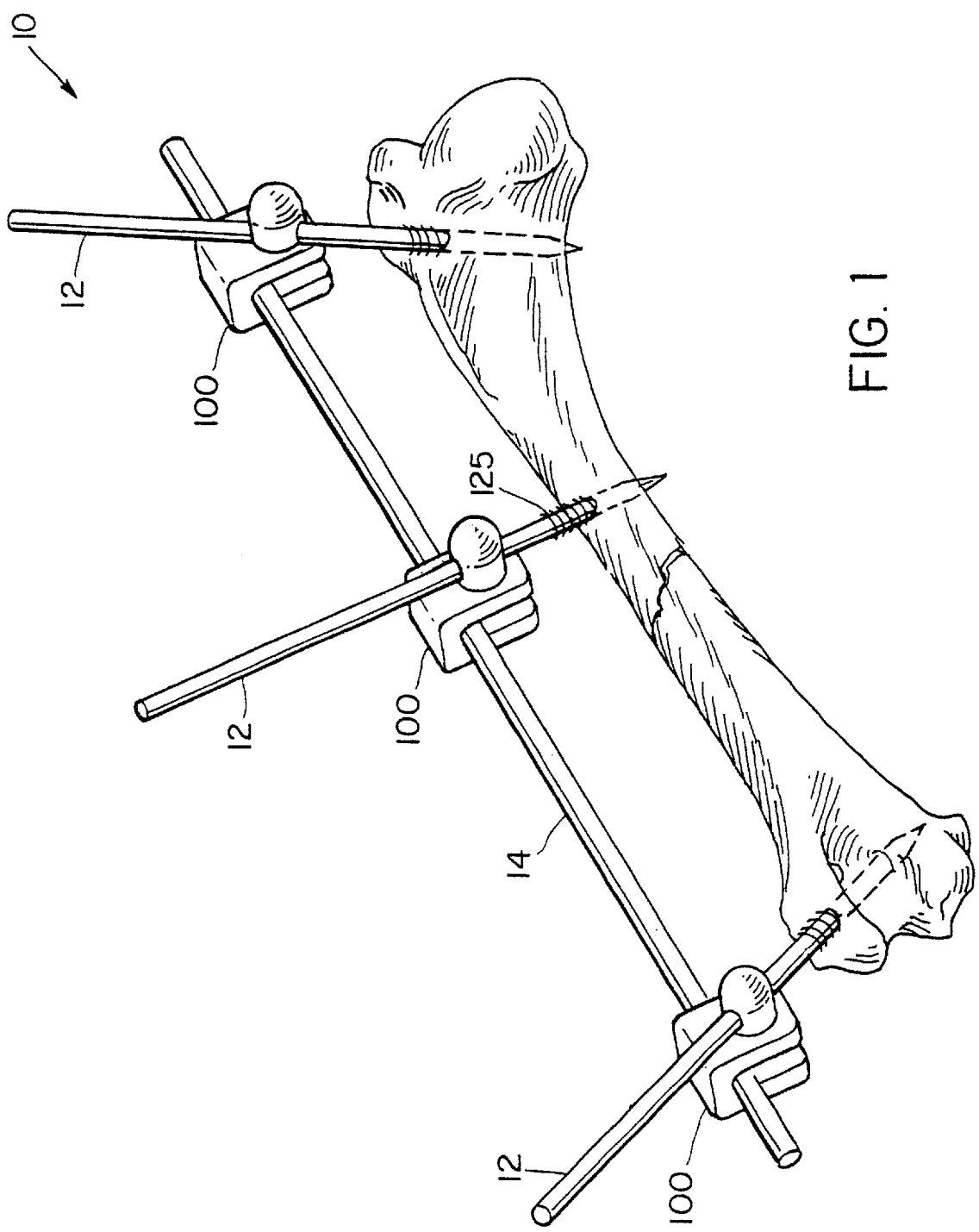
FIG. 1 is a perspective view of an external fixator clamp system including multiple fixator clamps that couple fixator pins to a common connecting rod to immobilize the fractured bone.

FIG. 1 is a perspective view of an external fixator system 10 incorporating clamps 100, which have been constructed according to the principles of the present invention. As is common in these systems 10, a number of the clamps 100 are used to connect fixator pins 12 to a connecting rod 14. The pins 12 are typically constructed from stainless steel and preferably have positive-profile threads 125. The fixator rod 14 may also be constructed from stainless steel, but alternatives such as carbon fiber or acrylic may be substituted. According to the invention, the clamps 100 may be constructed from 316 or 304 stainless steel, carbon fiber, or fiber-glass.

The inventive system has applications in a variety of environments. Low cost coupled with the fact that patient mobility is regained immediately after installation makes the system applicable in the veterinary setting. These qualities, however, make it also useful in certain human applications, for example, treatment on the battlefield or in third world countries.

The most extreme stresses occur at the pin-bone interface, which can cause premature loosening. It is therefore important to select pins of maximum stiffness. As pin stiffness is proportional to the fourth power of pin radius, positive-profile threaded pins are preferred. A positive-profile threaded pin has threads of greater diameter than the pin shaft, resulting in a stiffer pin, and increased pin-bone adhesion. These are preferred over negative-profile threaded pins which have threads cut into the shaft, and therefore have drastically reduced pin stiffness.

Figure 2:
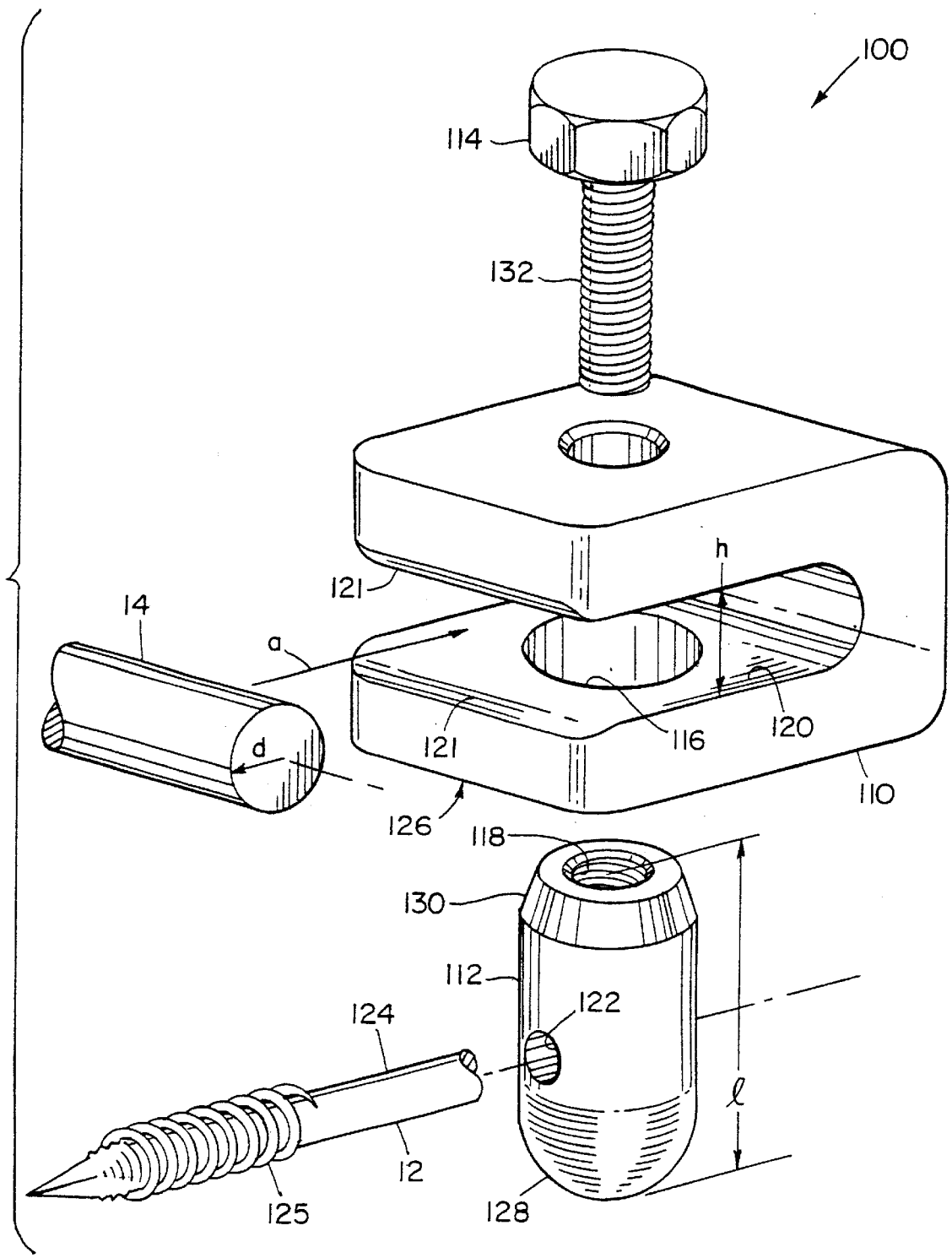
FIG. 2 is a perspective, exploded view of the fixator clamp of the present invention.

FIG. 2 is an exploded view of one of the inventive clamps 100. Generally, the clamp 100 comprises a clamp body 110, a pin connector 112 that receives the fixator pin 12, and some means for urging or drawing the pin connector 112 into a connector bore 116 so that the fixator pin 12 is braced against the clamp body 110. In the illustrated embodiment, the pin connector is engaged by a ⅜" long hex-head bolt 114 inserted from the distal side of the clamp body 110. The external 10–32 threads 132 of the bolt 114 mate with the internal threads 118 of the pin connector 112.

The clamp body 110 has a generally "U"-shaped cross-section defining a slot 120. The height h of the slot 120 is chosen so that the clamp body 110 may be transversely fitted over the rod 14, enabling the rod 14 to be inserted into the slot 120 in the direction of arrow a. The mouth of the slot 120 can have opposed chamfered surfaces 121 to facilitate the insertion. Since the clamp body 110 can transversely receive the rod, the clamp 100 is also applicable to other systems such as Ilizarov ring fixator rods along with type-two, -three fixator systems.

In the preferred embodiment, the height h of the slot 120 is machined to the outer diameter d of the connecting rod 14. This dimensioning ensures that there is a slight interference fit between the rod and the slot, limiting play in the clamp body 110-rod 14 interface even before the clamp is secured. Alternatively, the slot height h can be machined to be somewhat larger than the outer diameter d of the rod 14 or smaller, enabling the clamp to be snap fit over the rod 14. In this later case, the clamp body 110 flexes somewhat enabling the slot height h to marginally increase and accept the rod 14. The force necessary to install the clamp body, however, should not exceed the force that the typical surgeon can apply.

The pin connector 112 has a radially-extending pin bore 122 that receives the fixator pin 12. Preferably the pin bore 122 should be dimensioned to smoothly receive the connector pin 12, but without excessive play between the pin 12 and bore's inner walls. When the clamp 100 is fully constructed, the pin connector 112 is pulled into the connector bore 116 so that the shaft 124 of the pin 12 is braced against the proximal outer surface 126 of the clamp body 110.

In the preferred embodiment, the pin connector 112 has a dome-shaped proximal end 128 and is internally threaded 118 at its distal end. The dome shape ensures that the outer surface will not catch or snag during patient movement. The internal thread arrangement yields a low overall length 1 of the connector 112 which is helpful when constructing the clamp. The pin connector 112 additionally has a chamfered distal end 130, which engages the connector rod 114 when the clamp is fully constructed.

In alternative embodiments, the closed pin bore 122 is replaced by a slot-type bore yielding a hook-shaped member similar to that disclosed in the 08/643,512 application while retaining the rod-engaging surface 130 and short overall length disclosed here. The drawback associated with this embodiment, however, is the cost of machining the pin-slot, which is typically high due to its comparatively more complex shape relative to hole 122 and the concomitant reduction in rigidity of the connector due to the extended slot.

Figure 3:
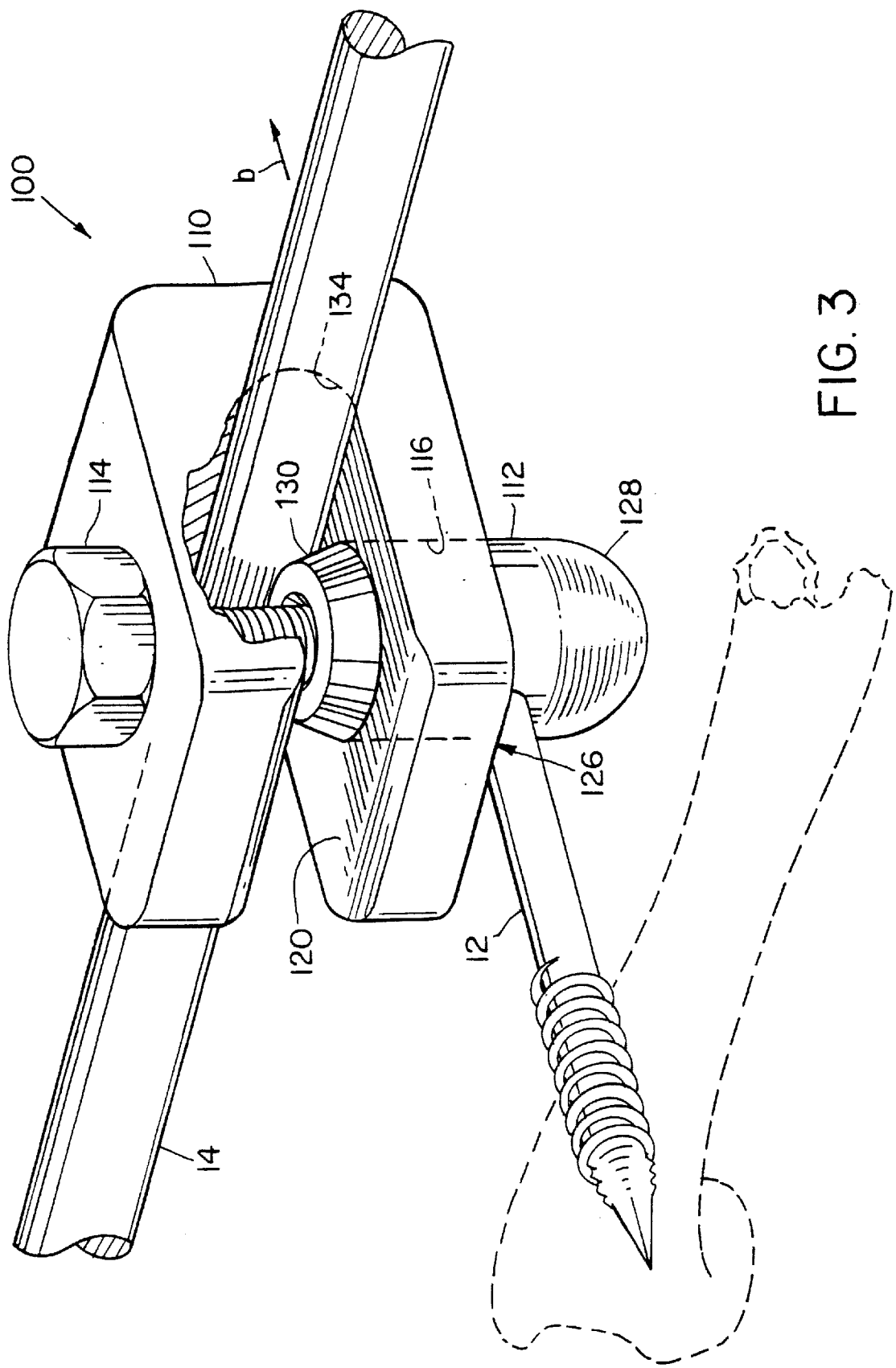
FIG. 3 is a perspective, partially cut-away view of the inventive fixator clamp, when constructed.

FIG. 3 is a perspective view of the constructed clamp 100 with a small cut-away to show the junction between the pin connector 112 and the connecting rod 14. Tightening the bolt 114 draws the pin 12 against the distal outer surface 126 of the clamp body 110. This action braces the pin against the clamp preventing the rotation of the pin connector 112 and thus the pin 12. Moreover, the pin 12 is prevented from moving axially with respect to connector 112.

Tightening the bolt 114 additionally draws the rod-engaging surface 130 of the connector 112 into engagement with the connecting rod 14. This interference has a number of effects that further prohibit any movement of the tightened clamp 100. First, friction between the rod-engaging surface 130 and the outer surface of the rod 14 further prevents any rotation of the pin connector 112. Additionally, the force exerted by the pin connector at this junction pushes the rod 14 in the direction of arrow b. This ensures that the rod 114 is seated against the back wall 134 of the slot 120 providing a good rigid mechanical junction between the connecting rod 114 and the clamp body 110 preventing rotation of the clamp body around or sliding along the connecting rod 14.

In the preferred embodiment, the clamp body 110 does not substantially squeeze-down on or close over the connecting rod when the bolt 114 is tighten. It is only the interference between the rod-engaging surface 130 and the rod 14 that prevents movement between the rod 14 and clamp 100.

Figure 4:
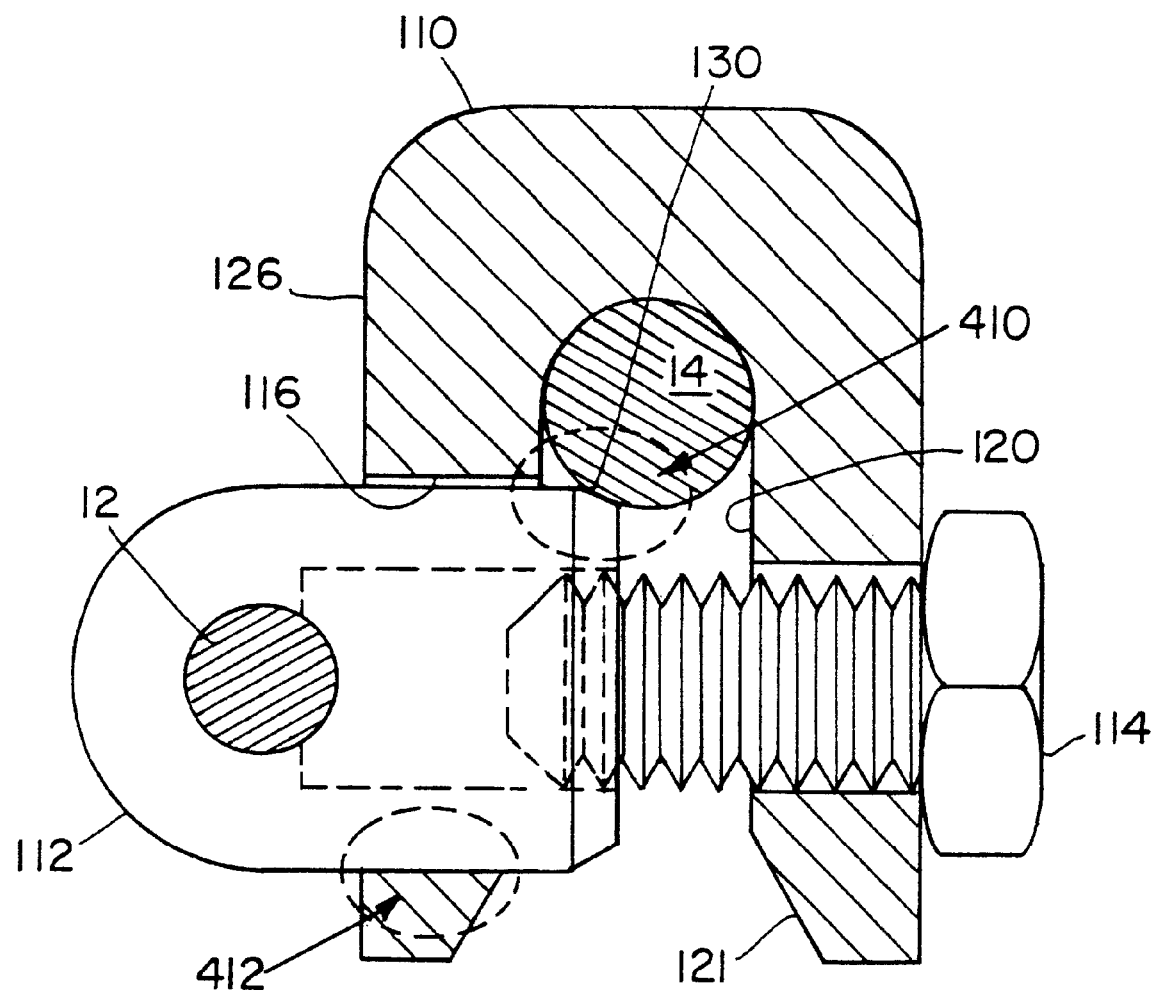
FIG. 4 is a cross-sectional view of the constructed fixator clamp identifying areas of contact between the pin connector, clamp body, and connecting rod.

FIG. 4 is a cross-sectional view illustrating the major points of contact that increase the rigidity of the constructed clamp 100 relative to those in the prior art. The first area of contact 410 is between the rod-engaging surface 130 and the outer surface of the connecting rod 14. This prevents rotation of the rod 14 with respect to the clamp body 110 and ensures the rod is fully seated in the slot 120. The force exerted by the rod 14 against the pin connector 112 additionally pushes the pin connector into engagement with the internal wall of the connector bore 116 at the second contact area 412. This further prevents the rotation of the pin connector 112 when loads are placed on the pin 112.

In other implementations of the pin connector 112, the pin bore 122 has a diameter which is large enough to accommodate a cannula, e.g., 3/16 inch. This modified connector is useful when using the clamp 100 as a guide for drilling and inserting the pins 12. The modified connector is installed in the clamp body 110, and the clamp body 110 is installed on the connecting rod 14. The cannula is inserted into the enlarged pin bore 122 and used to predrill through the soft tissue of the patient with a trocar to the bone. The positive profile pin is then inserted down through the cannula and installed in the bone. Once completed, the cannula is removed along with the modified connector replaced with one appropriate for the narrower diameter pins 12. The pin connector is then inserted into the clamp body 110 and then tightened to secure the pin 12 to the rod 14.

Figure 5A:
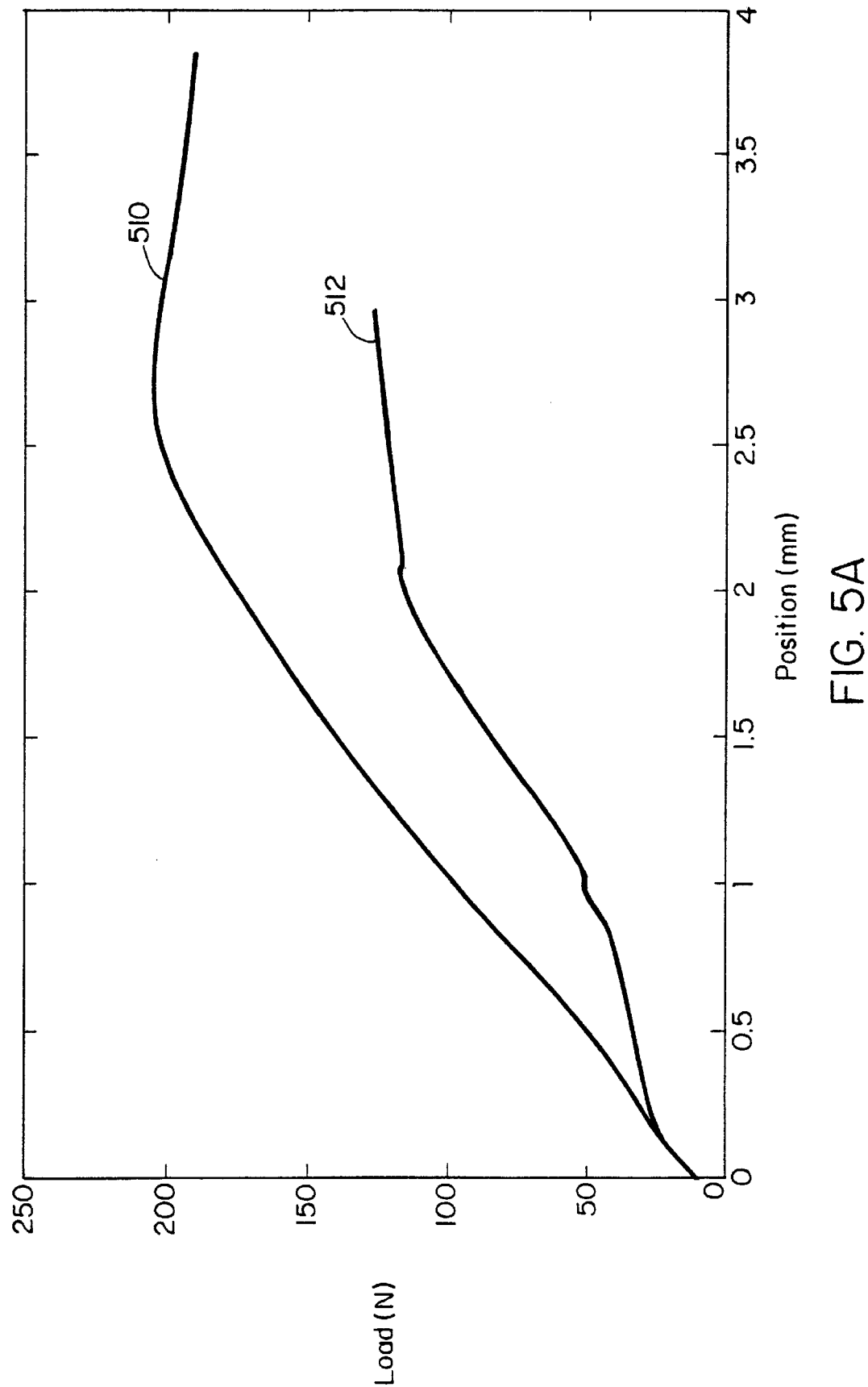
FIGS. 5A and 5B are plots of applied load as a function of displacement or position comparing the performance of the inventive clamps relative to commercially-available Kirschner-Ehmer clamps.
Figure 5B:
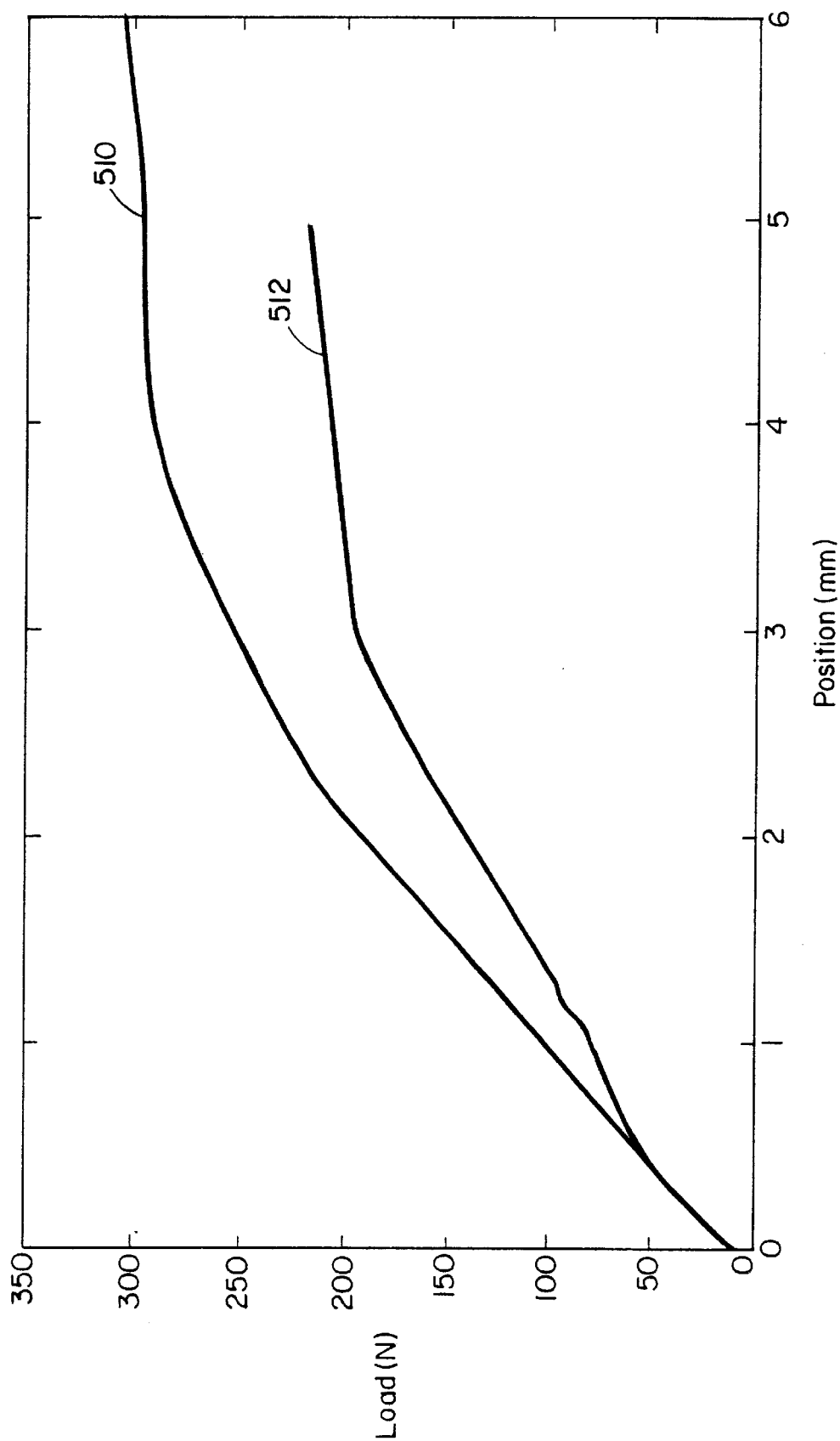

FIGS. 5A and 5B are graphs of load as a function of position comparing the performance of commercially-available Kirschner-Ehmer external fixator clamps relative to the fixator clamps of the present invention. The data was obtained using a specially designed jig that allowed application of clamps on a vertically-oriented 3/16 inch connecting rod supported with a triangular brace. A 3.2 millimeter pin was placed perpendicular, horizontal in the experimental set up, to the connecting rod. A device for applying a load to the 3.2 millimeter pin was constructed so that a concave 12 mm diameter bearing would apply a load on the 3.2 mm pin directly over a load cell. A servo-hydraulic mechanical testing machine was used for application of the force as well as collecting load and actuator pin data. The distance from the center of the clamp bolt to the applied force was 25 mm. A preload of 10 N force was applied on the 3.2 mm pin in a position ramp at a rate of 0.01 mm/sec. This continued for 4 mm.

FIG. 5A is data collected when the clamps were tightened to 40 inch-pounds. The inventive clamp (dark line) 510 showed a greater resistance to deformation than the commercially-available Kirschner-Ehmer clamp (grey line) 512. As illustrated in FIG. 5B, the invention's greater resistance to deformation also occurred when the clamps were tightened to 70 inch-pounds. Again, the inventive clamp (dark line) 510 showed a greater resistance to deformation than the commercially-available clamp (grey line) 512.

Figure 6A:
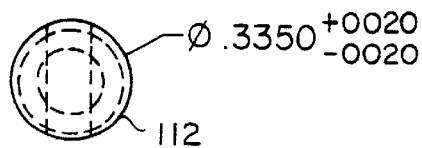
FIGS. 6A, 6B, and 6C are top, side, and bottom plan views of a connector showing the relevant dimensions in one implementation.
Figure 6B:
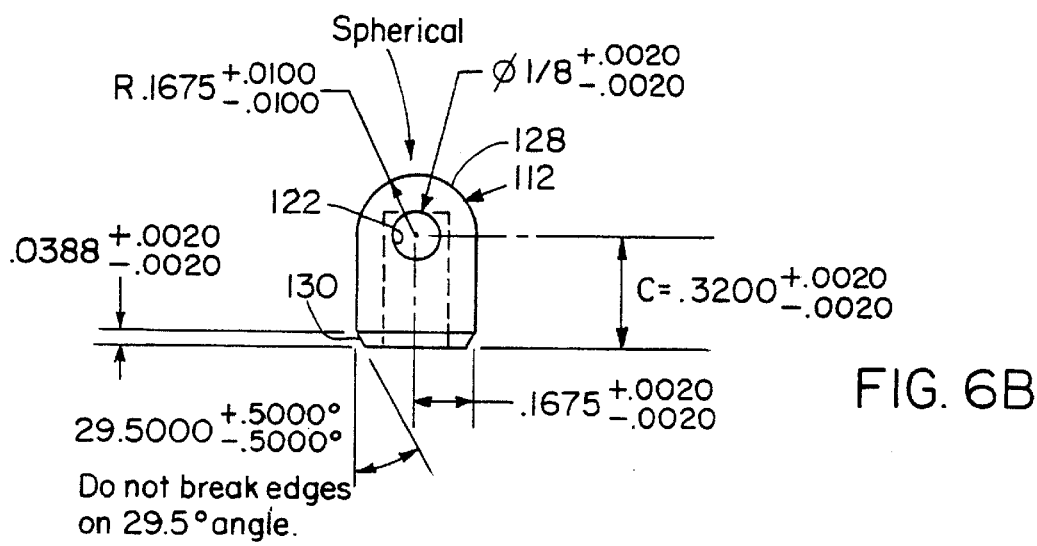
Figure 6C:
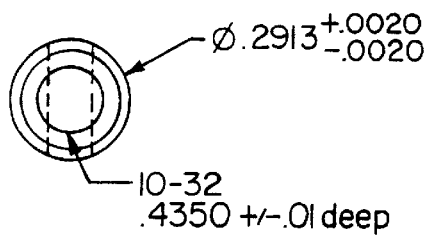

FIGS. 6A, 6B, and 6C show the dimensions for the connector 112. FIG. 6A is a top view showing the outer diameter of the connector. FIG. 6B is the side view of the connector 112 showing the 1/8 inch diameter pin bore 122. The distance c between the pin bore center and the bottom extent of the connector 112 is relevant to ensure that the rod-engaging surface 130 engages the connecting rod 14 while the pin 12, held in the bore 122, is simultaneously braced against the clamp body 110. The rod-engaging surface 130 is constructed by a chamfer on the end of the connector formed at an angle of 29.5. Finally, FIG. 6C shows the connector 112 from the bottom. This view shows the end diameter, the internal 10–32 internal threading, and its depth.

Figure 7:
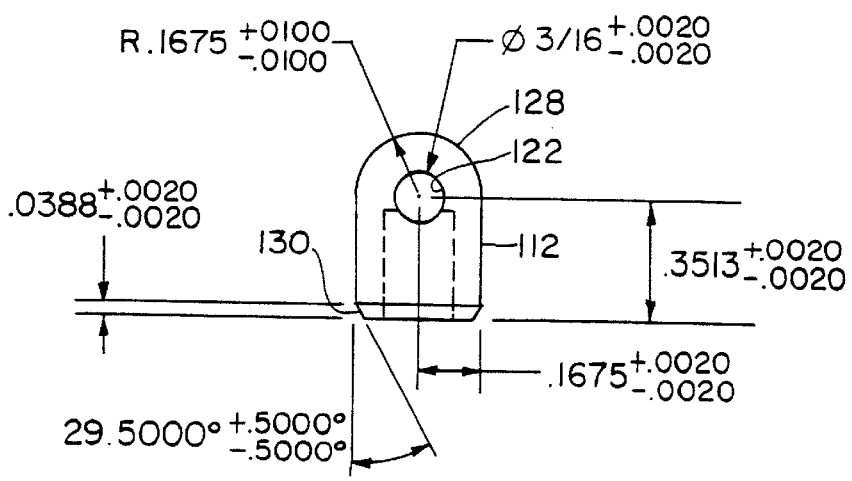
FIG. 7 is a side view showing the dimensions of the modified connector having a pin bore wide enough to accommodate a cannula.

FIG. 7 is a side view of the modified connector 112 showing the 3/16 inch diameter pin bore 122. This version is appropriate for use as a drill guide, the pin bore 122 being wide enough to receive the cannula.

Figure 8:
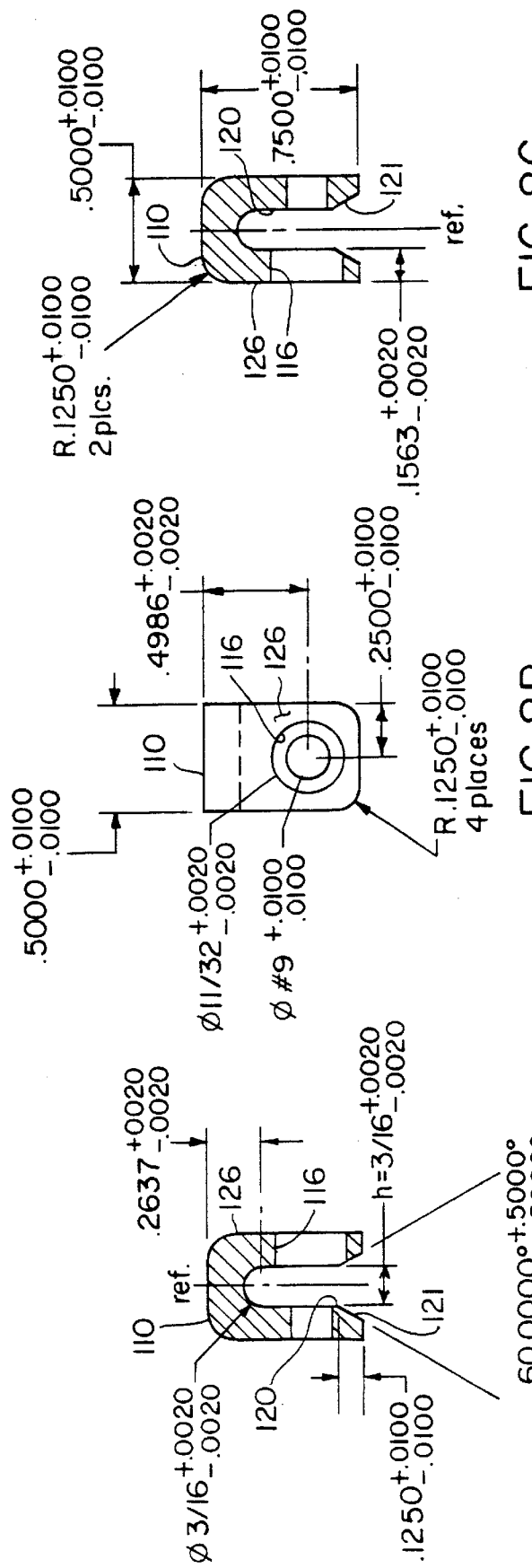
FIGS. 8A, 8B, and 8C are right side, top, and left side views of the clamp body showing the dimensions used in the construction of one implementation that is compatible with the connector shown in FIGS. 6A–6C.

FIGS. 8A, 8B, and 8C show the dimensions for the clamp body 110. FIG. 8A is a side view showing the dimensions of the slot. FIG. 8B is the top view. Finally, FIG. 8C is another side view showing the overall dimensions of the clamp body 110.

Figure 9:
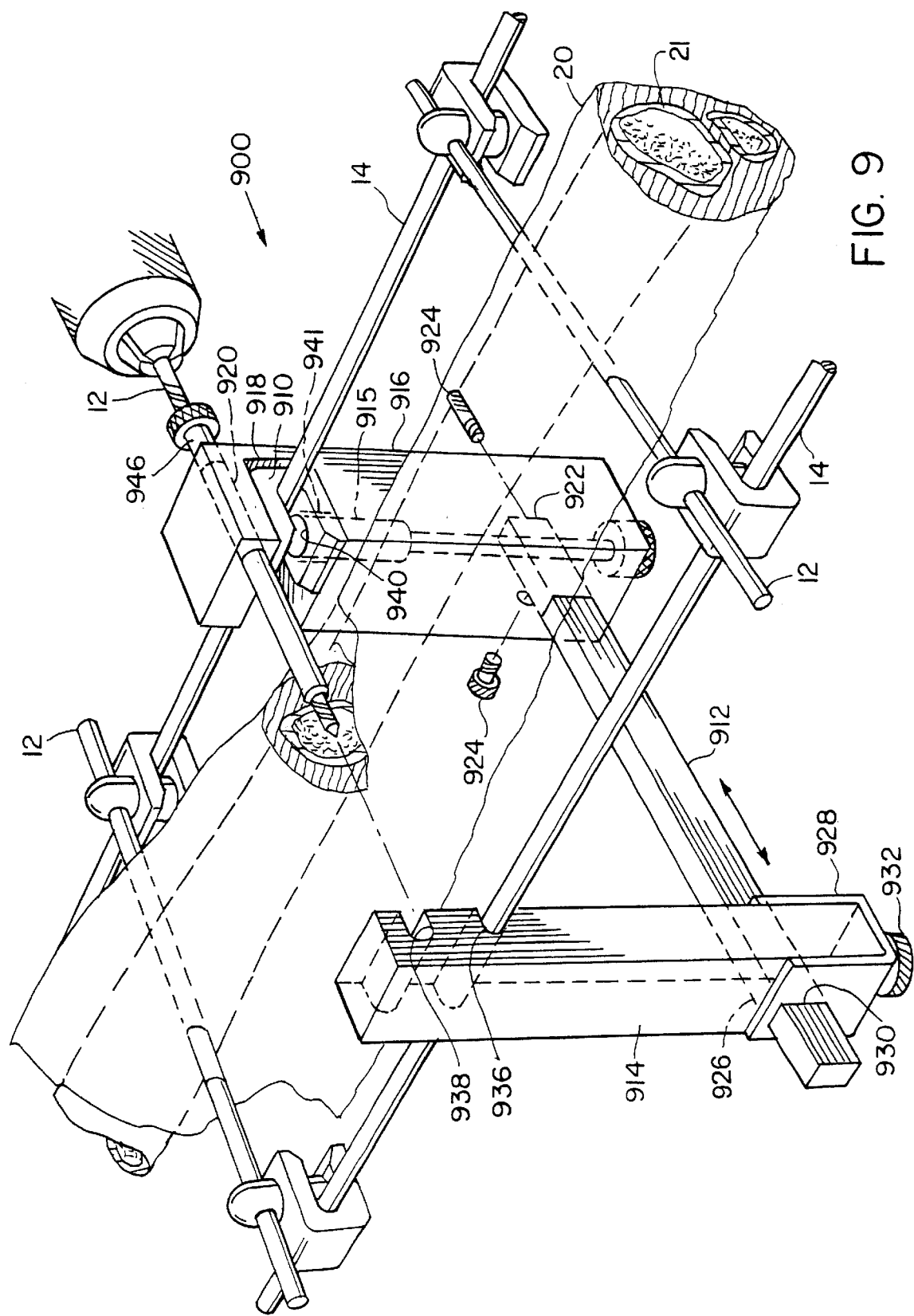
FIG. 9 is a perspective view of an aiming device of the present invention.

FIG. 9 is a perspective view illustrating the operation of an inventive aiming device that is compatible with the clamps 100 but may also be used with other clamp systems. The aiming device is most useful when installing pins 12 in type-two fixator systems in which the pins are secured to two connecting rods 12, one on either side of the limb 20.

The aiming device 900 comprises a frame constructed from a proximal transverse member 916, a connecting member 912 extending orthogonally away from the proximal transverse member 916, and a distal transverse member 914 that extends parallel to the proximal transverse member on the distant side of the limb 20 into which a pin 12 is to be installed.

The proximal transverse member 916 has a clamp slot 918 near the top end, in the orientation of FIG. 9. The clamp slot 918 houses a modified clamp body 910, which enables the proximal transverse member 916 to be installed onto the connecting rod 14. The modified clamp body 910 is retained in the clamp slot 918 by an extended thumb bolt 915 that has external threads 940 to engage a threaded connector bore 941 of the clamp body 910. A cannula bore 920 is formed in the proximal transverse member 916, above the clamp slot 918.

The orientation of the cannula bore 920 with respect to a connecting rod 14 held in the modified clamp 910 is such that an installed pin may be attached to the connecting rod via the clamp 100 described with reference to FIG. 2. That is, the distance between the center of the cannula bore 920 and the center of the slot in the modified clamp 910 is equal to the distance between the center of the pin bore 122 in the pin connector 112 and the center of the slot 120 in the clamp body 110 in the constructed clamp of FIG. 2.

In alternative embodiments, the cannula bore 920 is replaced with a sleeve arrangement. Such a sleeve can be ridgedly attached to the member or pivotable, continuously or only at discrete angles, to enable pin placement at various inclinations with respect to the connecting rods 14.

The connecting member 912 is received into a rectangular bore 922 in the bottom end of the proximal transverse member 916 in a mortise and tenon arrangement. The connecting member 912 is retained in the bore 922 with set screws 924.

The distal transverse member 914 extends perpendicularly away from the connecting member 912. A rectangular bore 926 is formed in the distal transverse member in which the connecting member 912 may slide to accommodate various tissue thicknesses of the patient's limb. The distal transverse member 914 has first and second slots 936, 938 for connecting it to the distant-side connecting rod in the type-two fixator system.

A clevis clamping member 928 fits over the bottom end of the distal transverse member 914, the connecting member 912 extending through transverse passages 930 through the clevis member's legs. A thumb screw passing through the clevis member 928 and engaging a bottom end of the distal transverse member 914 is tighten to push the clevis member over the distal member 914 and secure the connecting member 912 in the rectangular bore 926 of the distal member 914 and thereby arrest the sliding of the distal member on the connecting member.

Figure 10:
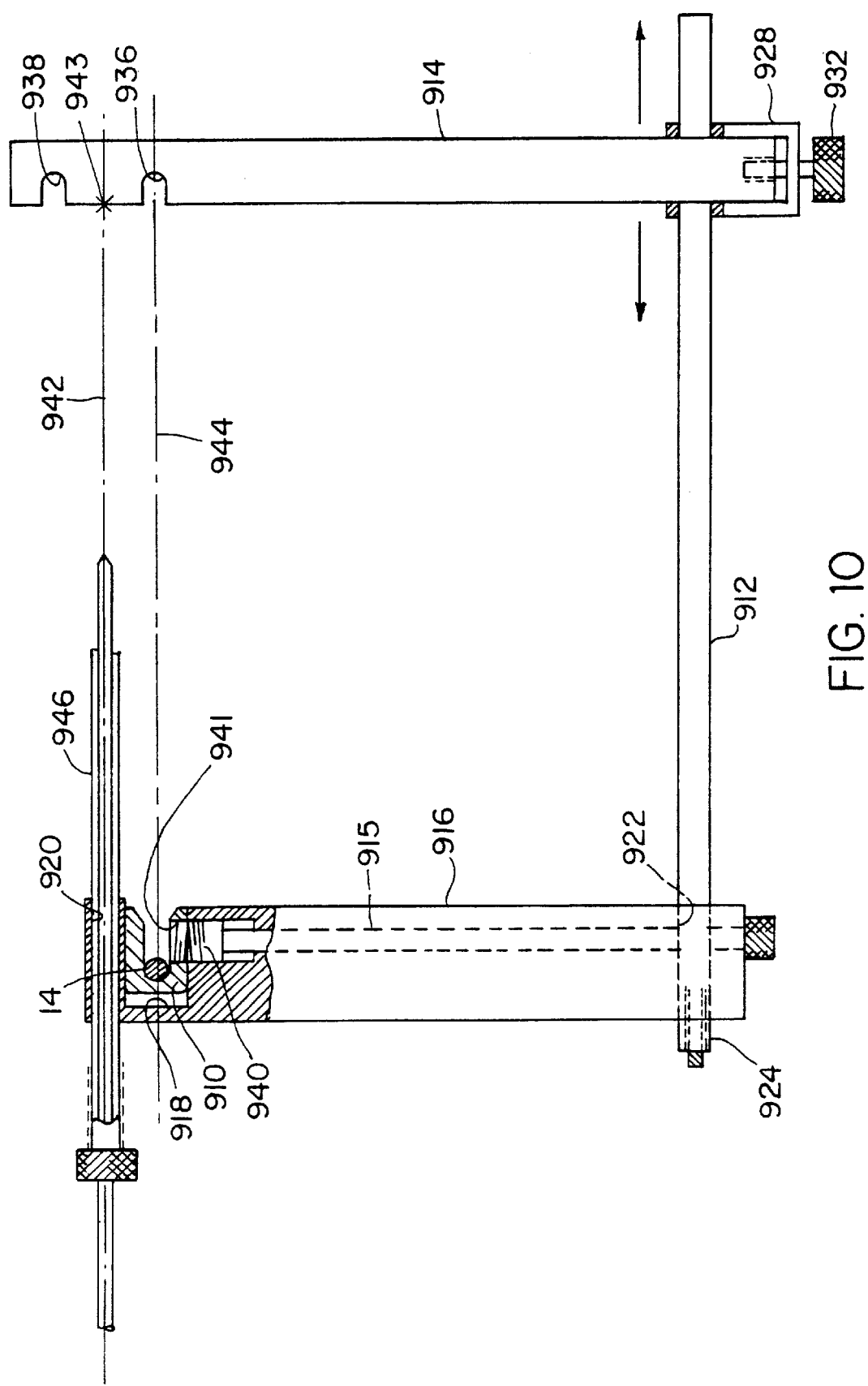
FIG. 10 is a side plan view of the inventive aiming device.

FIG. 10 is a plan view of the aiming device 900 better illustrating the location of the slots 936, 938 relative to the cannula bore 920 and modified clamp body 910. An axis 942 of the cannula bore 920 intersects the distal transverse member 914 at point 943, which is equidistant from the centers of the two slots 936, 938. The distance between the point 943 and the centers of either of the slots 936, 938 is the same as the distance between the axis of the cannula bore 920 and the center of the slot in the modified clamp body 910. This relationship is illustrated by line 944 which bisects the slot 936 and the clamp body 910. As a result of the relationship, one of the inventive clamps 100 described with reference to FIG. 2 may be installed on the distant-side connecting rod 14 and will be in an ideal position to attach a pin inserted through the cannula 946 and installed in the bone 21 of the limb 20. The two slots 936, 938 are provided to enable the clamp 100 to be installed above or below the distant-side connecting rod 14.

The inventive aiming device 900 holds the cannula 946 as it is inserted through the patient's soft tissue to the surface of the bone 21. A very narrow orthopedic pin may first be inserted, however, to properly locate the bone surface where the pin is to be set. Once the cannula has been inserted down to the bone, a pin 12 is inserted into the cannula and drilled into and through the bone 21 to the distant-side connecting rod 14. Once the pin is properly set, the aiming device and cannula are removed and the pin 14 is attached to both connecting rods using clamps 100.

In other applications, the proximal member 916 may be disconnected from the connecting member 912 by removing set screws 924. In this configuration, it is useful as an aiming device for type-one fixator systems.

While this invention has been particularly shown and described with references to preferred embodiments thereof, it will be understood by those skilled in the art that various changes in form and detail may be made therein without departing from the spirit and scope of the invention as defined by the appended claims.

We claim:

1. An aiming device for installing fixator pins, comprising:
    a frame attached to first and second connecting rods, the frame having at least one proximal slot for receiving the first connecting rod and two distal slots for receiving the second connecting rod, the distal slots adjusting the position of the fixator pin to be stalled either above or below the second connecting rod and allowing clamps having pin connectors to be installed to the second connecting rod, the pin connectors aligned with the position of installed fixator pins to attach the installed fixator pins to the second connecting rod; and
    a cannula mounted to the frame, the cannula having an opening that provides a guide for directing a fixator pin to be installed through a bone for fixating the bone between the connecting rods.

2. The aiming device described in claim 1, wherein the frame further comprises a bore formed in the frame.

3. The aiming device described in claim 1, wherein a proximal slot is formed in a clamp body held in the frame.

4. The aiming device described in claim 1, wherein the frame is expandable to accommodate various distances between the connecting rods.

5. The aiming device described in claim 1, wherein the frame comprises:
    a proximal member for attaching to the first connecting rod;
    a distal member for attaching to the second connecting rod; and
    a transverse member for connecting between the proximal and distal members.

6. The aiming device described in claim 5, wherein the proximal or distal member is slidable on the transverse member.

7. An aiming method for installing fixator pins, comprising:
    attaching a frame having a cannula for guiding a fixator pin to be installed to first connecting rod;
    selectably attaching the frame to second connecting rod to adjust the positioning of a fixator pin to be installed either above or below the second connecting rod;
    attaching clamps to the connecting rods, the clamps having pin connectors for receiving installed fixator pins, the pin connectors aligned with the fixator pin to be installed; and
    using an opening in the cannula to guide the fixator pin to the be installed through a bone to fixate the bone between the connecting rods.

8. The aiming method described in claim 10, further comprising sizing the frame to a distance between the connecting rods.

9. A method for installing a fixator pin comprising:
    providing a bone connected to at least one connecting rod;
    providing an aiming device having a frame and a cannula mounted to the frame;
    securing the frame to the at least one connecting rod;
    placing the cannula against the bone;
    inserting a fixator pin through the cannula to fixate the bone; and
    installing the fixator pin within the bone.

10. The method of claim 9 further comprising:

removing the aiming device from the at least one connecting rod; and clamping the fixator pin to the at least one connecting rod.

11. The method of claim 9 further comprising:

providing a trocar;

placing the cannula against a soft tissue surface surrounding the bone; and using the cannula and trocar to predrill through the soft tissue to the bone.

* * * * *